United States Patent [19]

Loev et al.

[11] Patent Number: 4,605,675

[45] Date of Patent: Aug. 12, 1986

[54] POLYENE COMPOUNDS USEFUL IN THE TREATMENT OF ALLERGIC RESPONSES

[75] Inventors: Bernard Loev, Scarsdale; Wan-Kit Chan, Yorktown Heights, both of N.Y.

[73] Assignee: USV Pharmaceutical Corp., Tarrytown, N.Y.

[21] Appl. No.: 787,843

[22] Filed: Oct. 16, 1985

[51] Int. Cl.[4] .................. A61K 31/05; A61K 31/075
[52] U.S. Cl. ..................................... 514/720; 514/731
[58] Field of Search ............................... 514/720, 731

[56] References Cited

PUBLICATIONS

Dawson et al. J. Med. Chem. (1981) 24 1214.

*Primary Examiner*—Stanley J. Friedman

[57] ABSTRACT

Polyene compounds represented by the formula

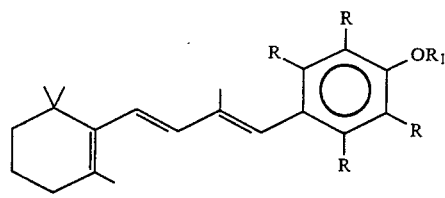

in which R is H or an alkyl group of from 1 to 5 carbon atoms, $R_1$ is H, lower alkyl of from 1 to 8 carbon atoms or aralkyl, and the pharmaceutically acceptable salts thereof.

The foregoing compounds have been found active in regulating phospholipases and as such possess therapeutic value in the treatment of inflammatory conditions.

2 Claims, No Drawings

POLYENE COMPOUNDS USEFUL IN THE TREATMENT OF ALLERGIC RESPONSES

BACKGROUND OF THE INVENTION

The present invention relates to polyene compounds and more particularly to dienoic compounds derived from aryl intermediates with the general formula:

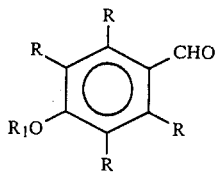

where

R is H or lower alkyl of from 1 to 5 carbon atoms; and $R_1$ is H, lower alkyl of from 1 to 8 carbon atoms or aralkyl.

Related prior art includes the following references:

A synthesis of 2,3,6-trimethyl-p-anisaldehyde is described in U.S. Pat. No. 4,105,681.

M. I. Dawson, et al. (*J. Med. Chem.*, 1981, 24, 1214) described the synthesis of (E)-1-(4-carbethoxyphenyl)-2-methyl-4-(2,2,6-trimethylbicyclo-[4.1.0]hept-1-yl)-1,3-butadiene and analogs and reported their activity in an assay for the inhibition of tumor promoter-induced mouse epidermal ornithine decarboxylase.

SUMMARY OF THE INVENTION

The present invention is directed to polyene compounds of the general formula

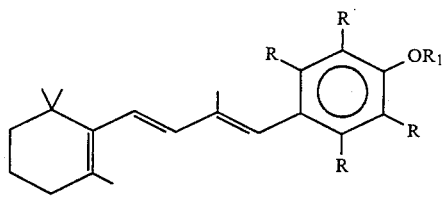

in which R is H or an alkyl group of from 1 to 5 carbon atoms, $R_1$ is H, lower alkyl of from 1 to 8 carbon atoms or aralkyl, and the pharmaceutically acceptable salts thereof.

DETAILED DESCRIPTION OF THE INVENTION

The compound of this invention can be prepared from known polyolefinic materials, e.g., aromatic aldehydes, employing known synthetic procedures or from analogous polyolefinic compounds which can be prepared in accordance with methods known by those skilled in the art.

The preferred method of synthesizing the compounds of the invention is described in the Example that follows.

EXAMPLE 1-(4-Methoxy-2,3,6-trimethylphenyl)-2-methyl-4-(2,6,6-trimethyl-1-cyclohexen-1-yl)butadiene

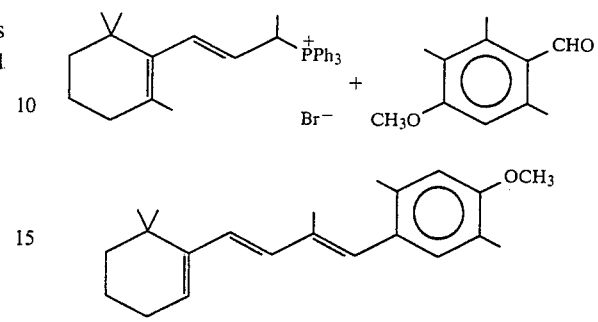

A solution of [4-(2,6,6-trimethyl-1-cyclohexen-1-yl)-3-buten-2-yl]triphenylphosphonium bromide (prepared from 17.2 g of 4-(2,6,6-trimethyl-1-cyclohexen-1-yl)-3-buten-2-ol and 30.4 g of triphenylphosphonium hydrogen bromide in 150 mL of N,N-dimethylformamide (DMF)) was stirred under nitrogen in an ice bath and NaH (4.25 g, 50% oil dispersion) was added in portions. The mixture was stirred in the cooling bath for an additional hour and a solution of 2,3,6-trimethyl-p-anisaldehyde (15.8 g, 0.089 mol) in 50 mL of DMF was added dropwise within 15 min. The resulting mixture was stirred at room temperature for 18 hrs and heated to 50°–60° C. for 1½ hrs. After cooling, the mixture was poored into 3 liters of water and extracted with hexane. The hexane extract was washed with 400 mL of a MeOH:$H_2O$ mixture (6:4, v/v) and water (400 mL). After drying over $Na_2SO_4$, the solvent was evaporated in vacuo to give 24.1 g of crude product as a brown oil. The pure product was obtained as a pale yellow oil from vacuum distillation of the crude product, bp. 152°–153° C. (0.075 mm of Hg); MS (CI): 339 (m++1).

Compounds of this invention display activities in regulating phospholipases and as such possess therapeutic value in the treatment of inflammatory conditions.

Inflammatory responses to a variety of offending stimuli are promoted by products of arachidonic acid metabolism. These products include leukotrienes (SRS-A), prostaglandins, prostacyclin and its metabolites, and thromboxanes. No matter what combination of products results from passage of substrate down the branches of this complex cascade, the initial step involves the release of arachidonic acid from phospholipids or from triglycerides containing this long-chain fatty-acid. The enzymes catalyzing such release of arachidonic acid are:

(a) phospholipase C followed by diglyceride lipase;

(b) phospholipase $A_2$, either soluble or membrane-bound; and (c) a lipase able to degrade triglycerides that contain arachidonic acid.

The following protocol describes a means for testing the inhibitory effect of these compounds on Phospholipase $A_2$ ($PLA_2$).

PROTOCOL

In Vitro Assay For Inhibitors of Phospholipase $A_2$ Assayed at pH 7.0 ($PLA_2$)

The $PLA_2$ employed in this screen is obtained by aggregation of purified rat platelets. In the enzyme assay phosphatidylcholine having $^{14}$C-labeled palmitate residues at $R_1$ and $R_2$ is employed as substrate. $PLA_2$ acts by cleaving the $R_2$ fatty acid ester bond yielding free fatty acid and lysophosphatidylcholine as follows:

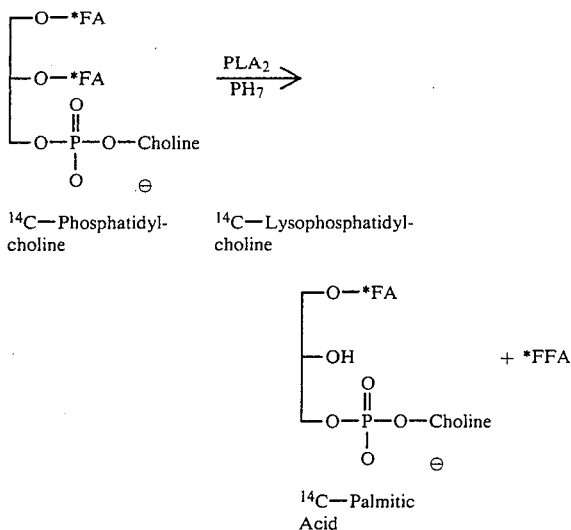

Following completion of the reaction, the assay medium is acidified and extracted with hexane, which takes up unreacted substrate and free fatty acid product. The hexane extract is passed over a short silica column which retains 99% of the phosphatidylcholine. The $^{14}$C-labeled palmitic acid is not retained (90% recovery in eluate) and is collected directly in scintillation counting vials. The released palmitic acid is conveniently quantitated by liquid scintillation spectrometry.

The compound was tested at 100 μM in a buffer containing 0.3 mM unlabeled phosphatidylcholine (PC), 20–30,000 cpm of $^{14}$C(CPC), 100 μM NaCl, 1 mM $CaCl_2$ and 50 mM tris-HCl adjusted to pH 7.2 with 1N NaOH. This resulted in a buffer at pH 7.2. The temperature of the buffer was maintained at a temperature of 37° C. The reaction was initiated by addition of the enzyme and it was terminated 30 minutes later by the addition of 100 ml of 1N HCl.

Following acidification, the sample was extracted with 2 mL of 2-propanol and 2 mL of hexane, vortexed and allowed to stand until the phases separated. Free fatty acids (FFA) and some unreacted substrate were taken up in the isopropanol-saturated hexane. The hexane phase of the extraction mixture was transferred to a short silica gell column which retained reacted PC but not the FFA. The column effluent was collected directly in scintillation vials. The columns were washed once with an additional 2 mL of hexane. The radio labeled FFA were quantitated by liquid scintillation spectrometry.

The compound of the Example showed a phospholipase $A_2$ inhibition activity of 58 μM at $I_{50}$ (Standard used: all-trans retinoic acid: 32% I at 100 μM).

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is intramuscularly, intravenously or subcutaneously. For parenteral administration, they may be used in the form of a sterile solution containing other solutes, for example, enough saline or glucose to make the solution isotonic. When applied topically for treating skin disorders, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally.

What is claimed is:

1. A therapeutic composition for the treatment of inflammatory conditions and allergic responses in a human host, in combination with at least one pharmaceutically acceptable extender, a therapeutically effective amount of a compound of the formula

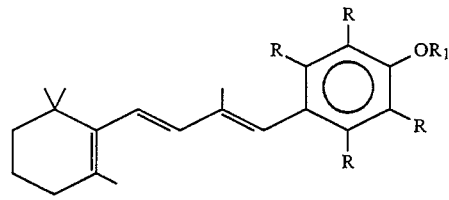

in which R is H or an alkyl group of from 1 to 5 carbon atoms, $R_1$ is H, lower alkyl of from 1 to 8 carbon atoms or aralkyl, or a pharmaceutically acceptable salt thereof.

2. A method for treating inflammatory conditions and allergic responses in a human host which comprises administering to said host a therapeutically effective amount of at least one compound of the formula

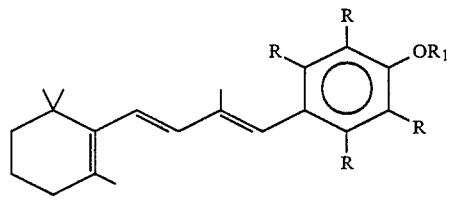

in which R is H or an alkyl group of from 1 to 5 carbon atoms, $R_1$ is H, lower alkyl of from 1 to 8 carbon atoms or aralkyl, or a pharmaceutically acceptable salt thereof.

* * * * *